(12) United States Patent
Rocci et al.

(10) Patent No.: US 8,911,445 B2
(45) Date of Patent: Dec. 16, 2014

(54) REAMER GUIDE SYSTEMS AND METHODS OF USE

(75) Inventors: Mirko Rocci, Solothurn (CH); Michael Jeffry Weber, Bettlach (CH)

(73) Assignee: DePuy Sysnthes Products, LLC, Raynham, MA (US)

( * ) Notice: Subject to any disclaimer, the term of this patent is extended or adjusted under 35 U.S.C. 154(b) by 111 days.

(21) Appl. No.: 13/015,804

(22) Filed: Jan. 28, 2011

(65) Prior Publication Data
US 2012/0197261 A1 Aug. 2, 2012

(51) Int. Cl.
*A61B 17/17* (2006.01)
*A61B 17/80* (2006.01)
*A61B 17/16* (2006.01)

(52) U.S. Cl.
CPC ..... *A61B 17/1739* (2013.01); *A61B 2017/1782* (2013.01); *A61B 17/8061* (2013.01); *A61B 17/1686* (2013.01)
USPC .......................................... 606/96; 606/86 R

(58) Field of Classification Search
CPC ........... A61B 17/1686; A61B 17/1739; A61B 17/8061
USPC ........................ 606/79–80, 86 R–87 R, 96–98
See application file for complete search history.

(56) References Cited

U.S. PATENT DOCUMENTS

| | | | |
|---|---|---|---|
| 5,147,367 A * | 9/1992 | Ellis | 606/96 |
| 5,507,801 A * | 4/1996 | Gisin et al. | 606/86 R |
| 5,951,561 A | 9/1999 | Pepper et al. | |
| 6,129,729 A * | 10/2000 | Snyder | 606/916 |
| 6,179,839 B1 * | 1/2001 | Weiss et al. | 606/281 |
| 6,344,043 B1 * | 2/2002 | Pappas | 606/96 |
| 7,141,074 B2 * | 11/2006 | Fanger et al. | 606/80 |
| 2003/0220641 A1 | 11/2003 | Thelen et al. | |
| 2003/0220646 A1 * | 11/2003 | Thelen et al. | 606/79 |
| 2004/0193173 A1 * | 9/2004 | Knopfle et al. | 606/96 |
| 2005/0203523 A1 * | 9/2005 | Wenstrom et al. | 606/79 |
| 2006/0149249 A1 * | 7/2006 | Mathoulin et al. | 606/69 |

(Continued)

FOREIGN PATENT DOCUMENTS

| | | | | |
|---|---|---|---|---|
| DE | 20 2007 01315 | | 4/2008 | |
| EP | 281763 A2 * | | 9/1988 | ............ A61B 17/56 |
| EP | 0 506 213 | | 9/1992 | |
| EP | 1 570 793 | | 9/2005 | |

(Continued)

OTHER PUBLICATIONS

International Patent Application No. PCT/US2011/022842: International Search Report and Written Opinion dated Dec. 2, 2011, 20 pages.

*Primary Examiner* — Eduardo C Robert
*Assistant Examiner* — Eric S Gibson
(74) *Attorney, Agent, or Firm* — Wayne C. Jaeschke, Jr.

(57) ABSTRACT

A reamer guide system may include a reamer guide that is configured to guide a reamer to at least two bones that are to be reamed to form a countersink. The reamer guide may be configured to temporarily couple to the at least two bones that are to be reamed so as to prevent substantial separation of the at least two bones during the reaming. The reamer guide system may further include a positioning aid that is configured to receive a locating element. The locating element is configured to temporarily couple to a target location adjacent the bones that are to be reamed. The reamer is configured to receive the locating element and advance along the locating element to the target location.

26 Claims, 15 Drawing Sheets

(56) References Cited

U.S. PATENT DOCUMENTS

| | | | |
|---|---|---|---|
| 2007/0012816 A1* | 1/2007 | Kaup et al. | 242/615 |
| 2007/0055286 A1* | 3/2007 | Ralph et al. | 606/96 |
| 2007/0191852 A1 | 8/2007 | Shimko et al. | |
| 2007/0244486 A1 | 10/2007 | Hogg et al. | |
| 2009/0076555 A1* | 3/2009 | Lowry et al. | 606/280 |
| 2009/0234396 A1 | 9/2009 | Medoff | |
| 2009/0275946 A1* | 11/2009 | Duncan | 606/62 |
| 2009/0318927 A1* | 12/2009 | Martin et al. | 606/96 |

FOREIGN PATENT DOCUMENTS

| | | |
|---|---|---|
| EP | 1 699 367 | 9/2006 |
| EP | 2 002 793 | 12/2008 |
| EP | 2 168 507 | 3/2010 |
| FR | 2 935 255 | 3/2010 |
| GB | 2 401 053 | 11/2004 |
| WO | WO 03/057087 | 7/2003 |
| WO | WO 2005/060839 | 7/2005 |
| WO | WO 2007/061983 | 5/2007 |

* cited by examiner

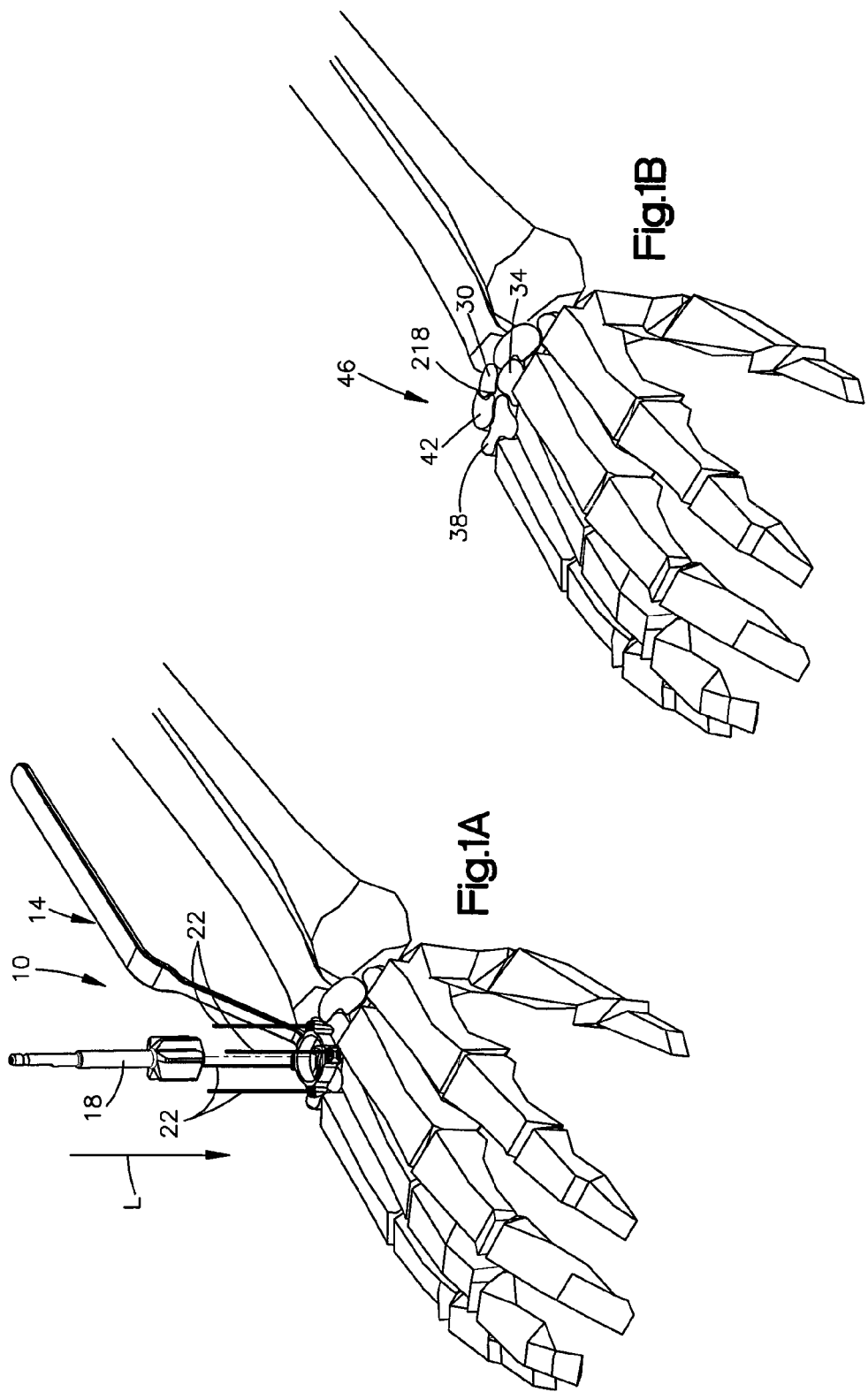

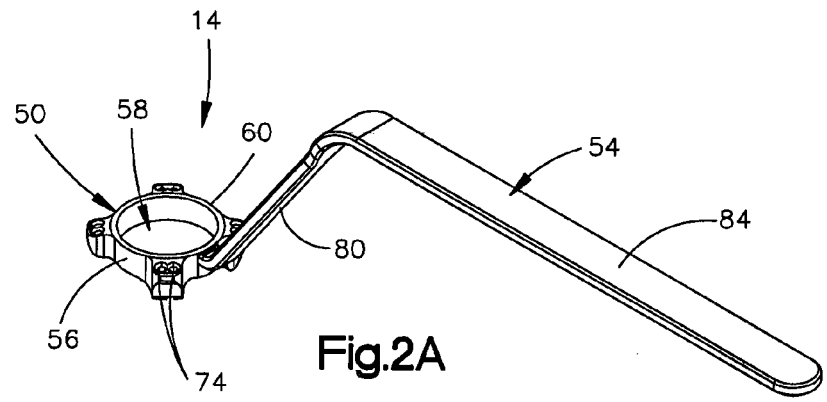
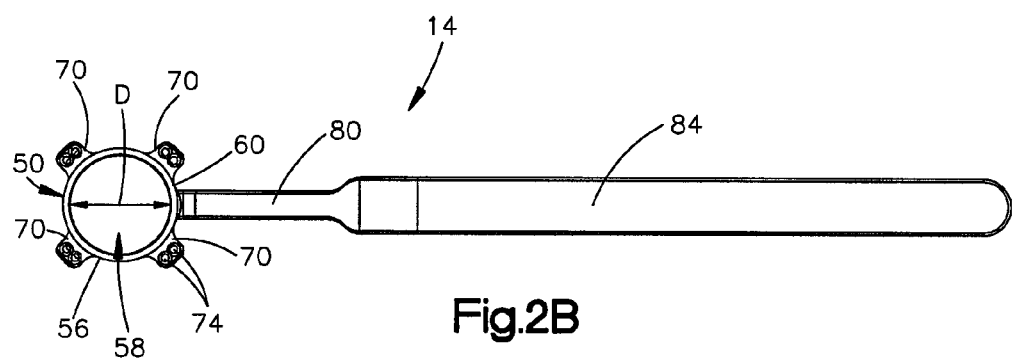
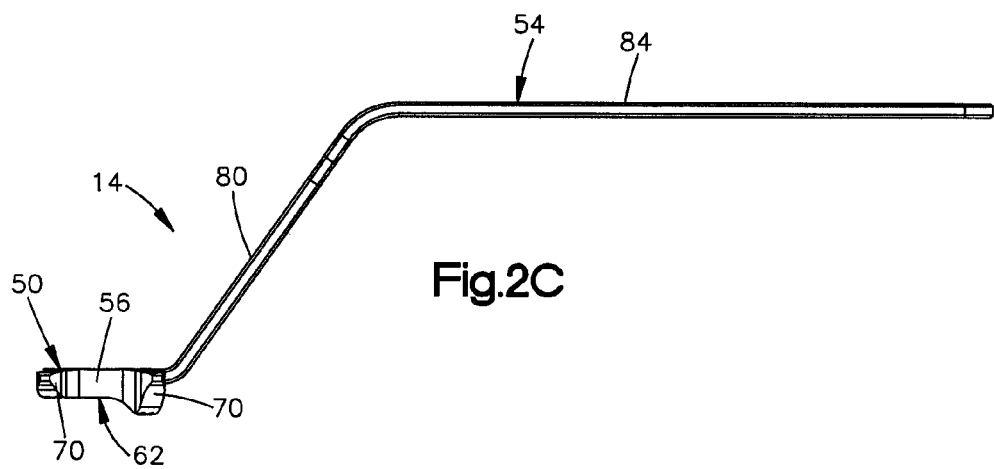

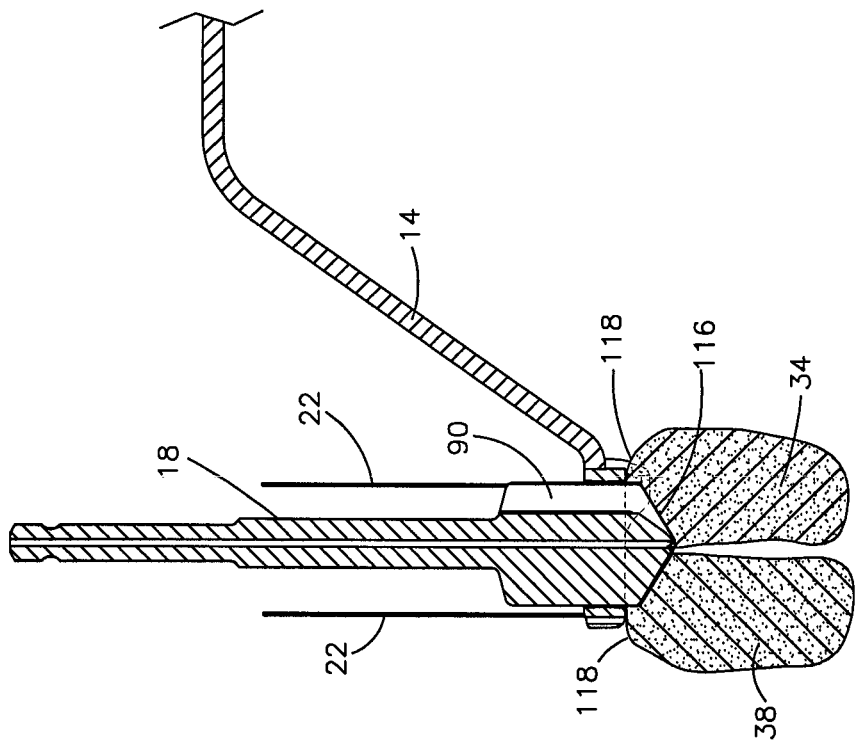
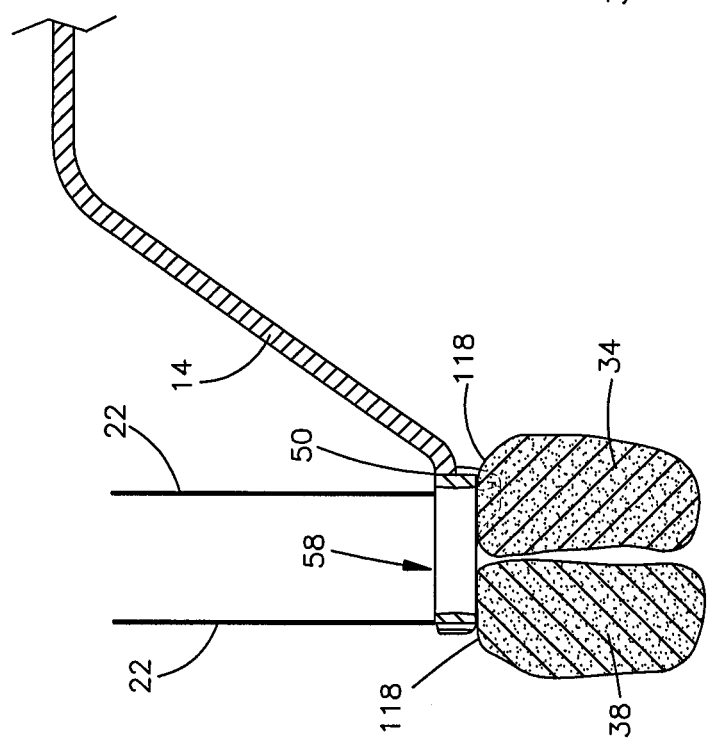

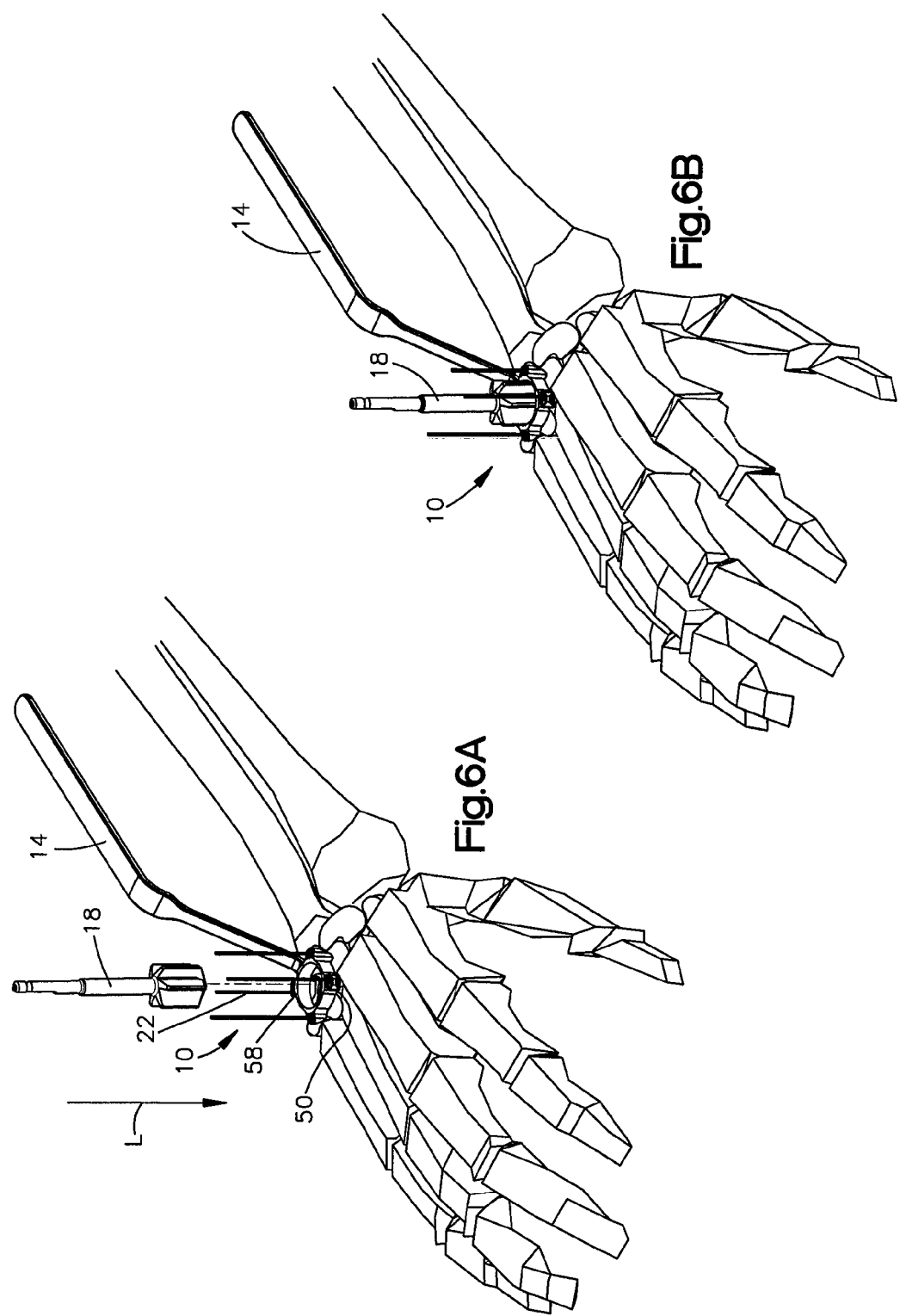

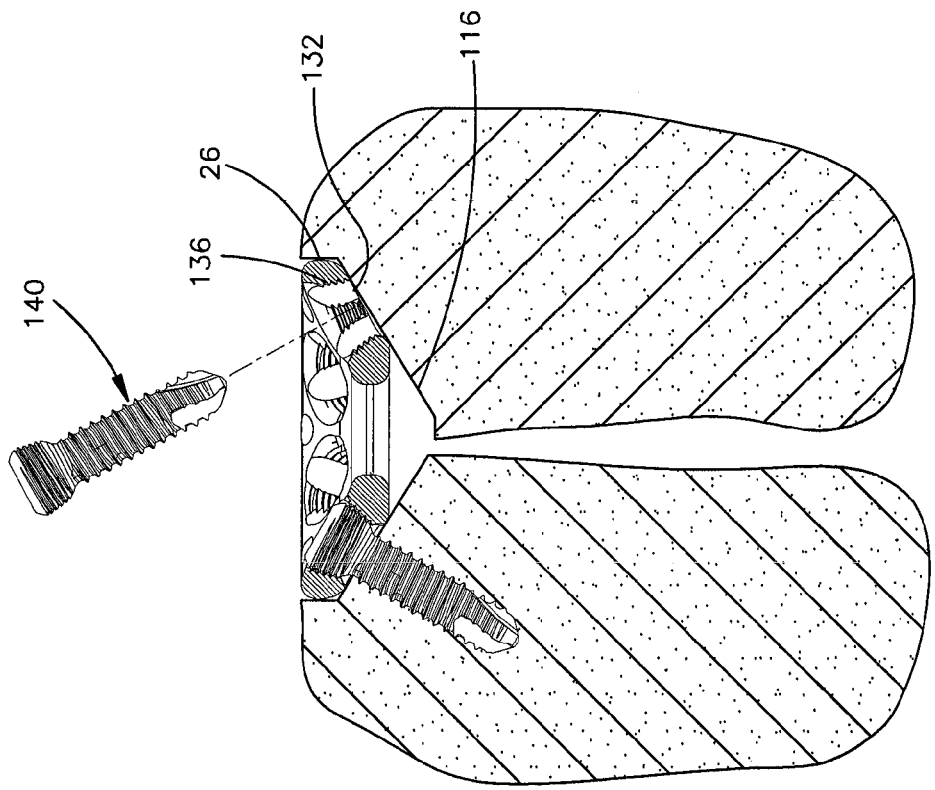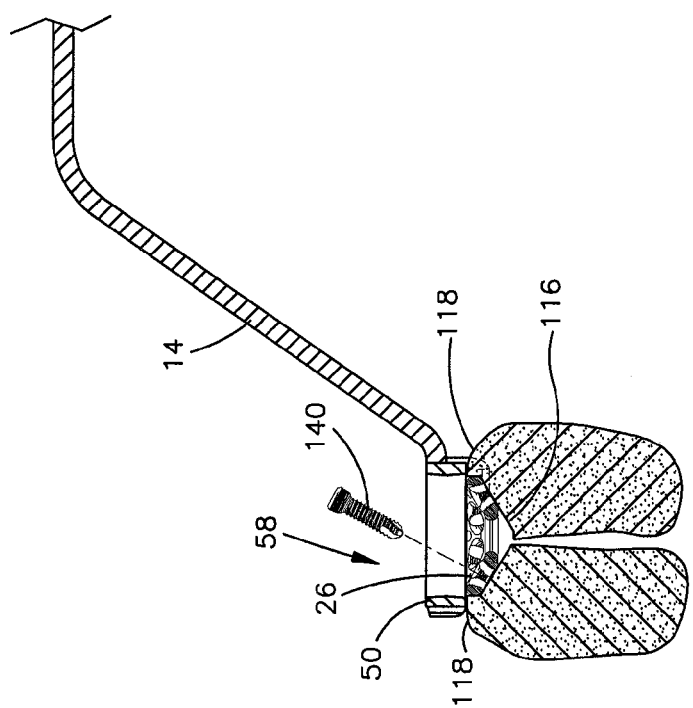
Fig.6D
Fig.6C

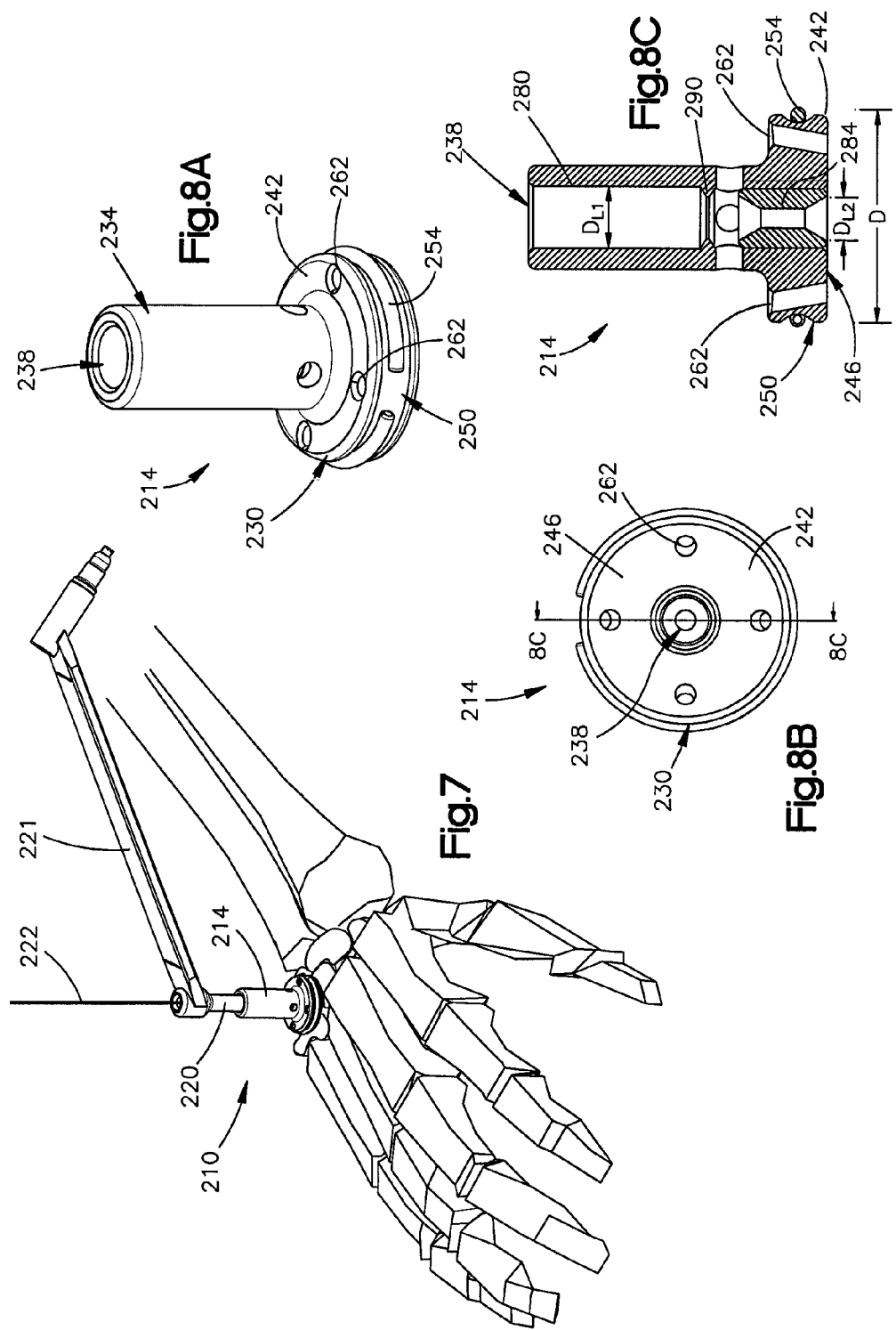

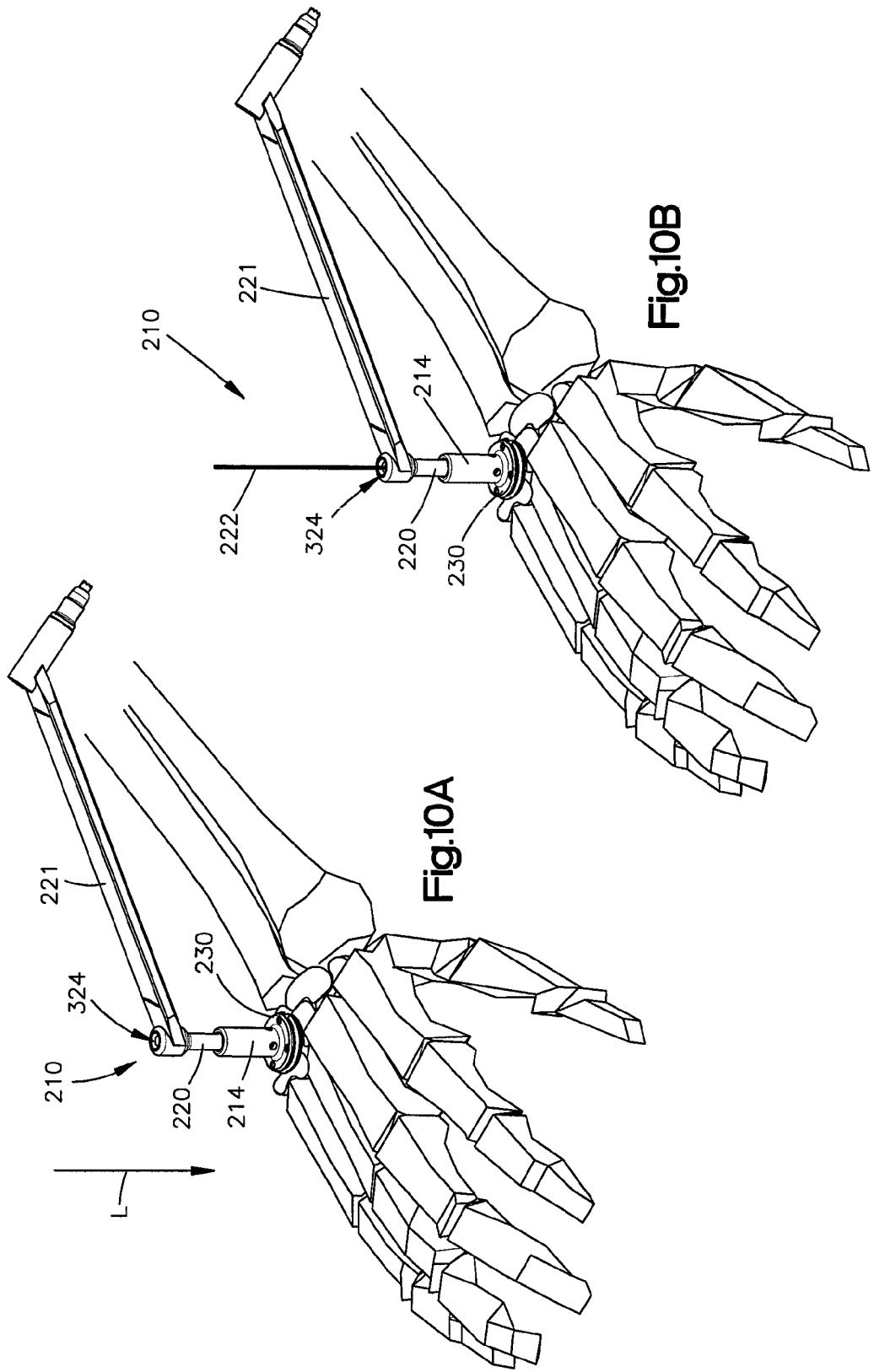

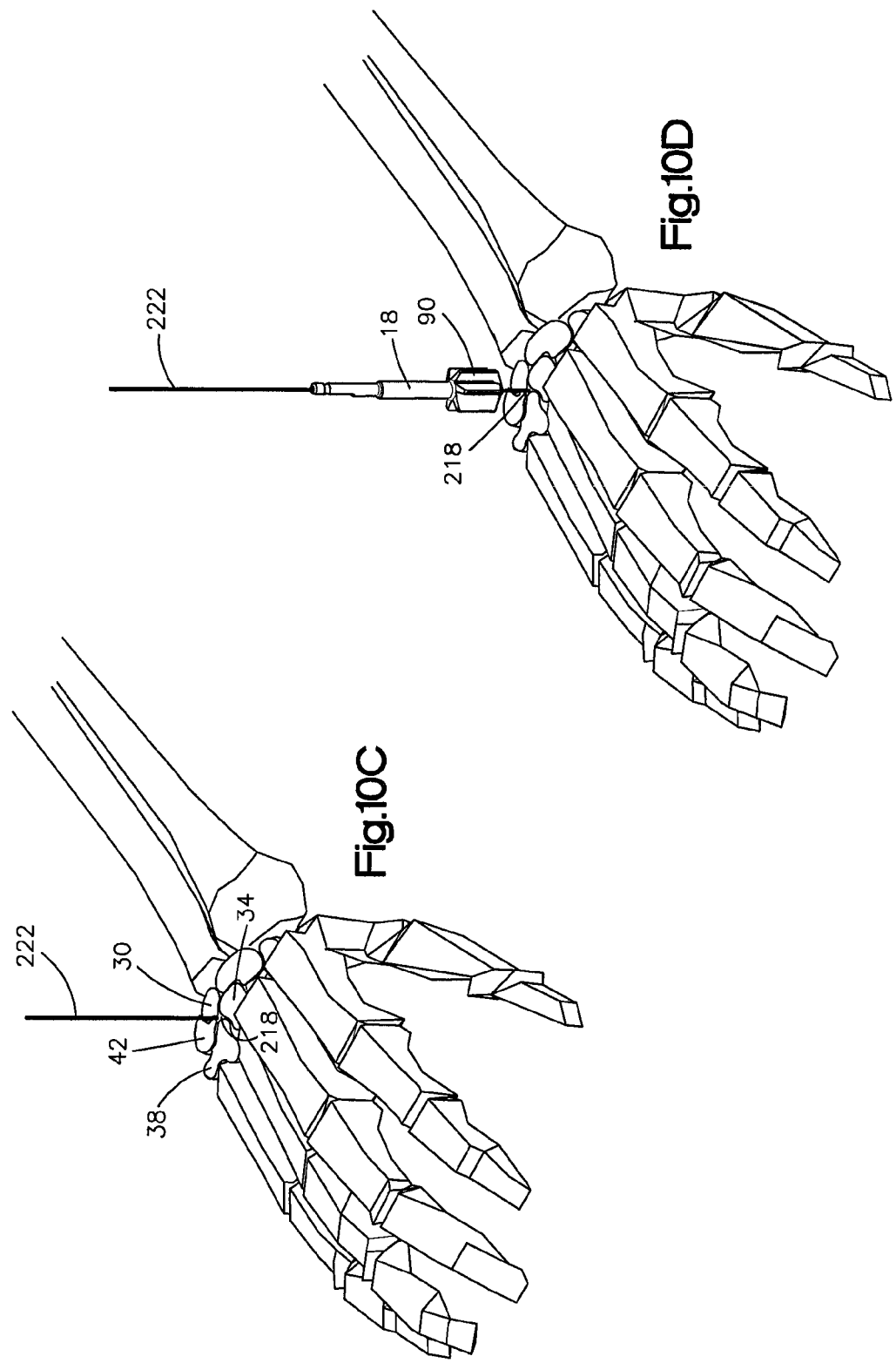

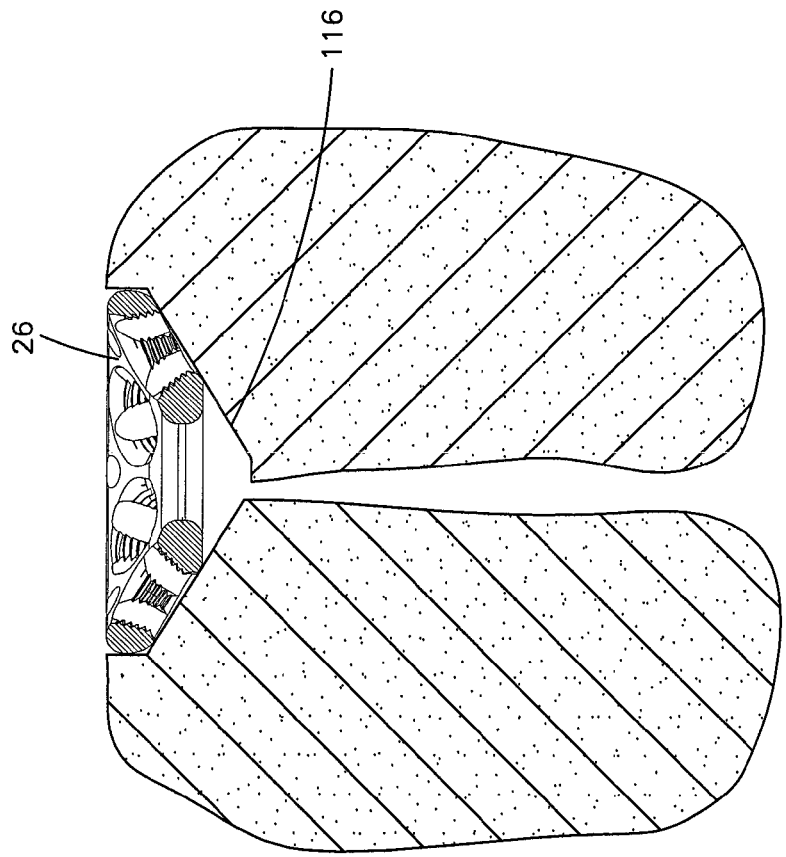
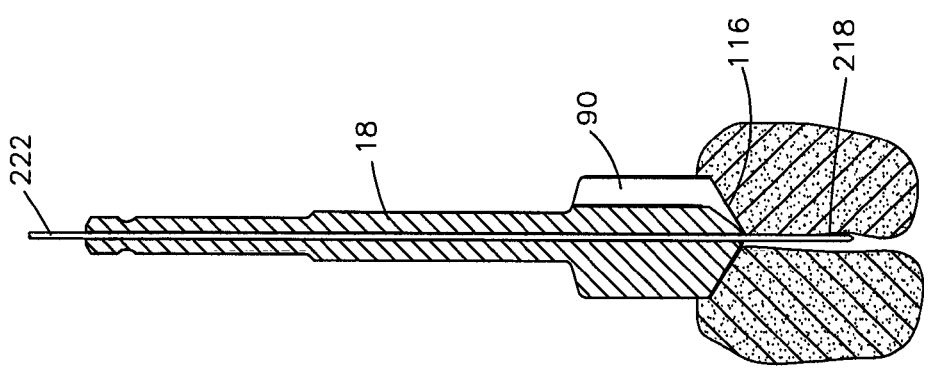

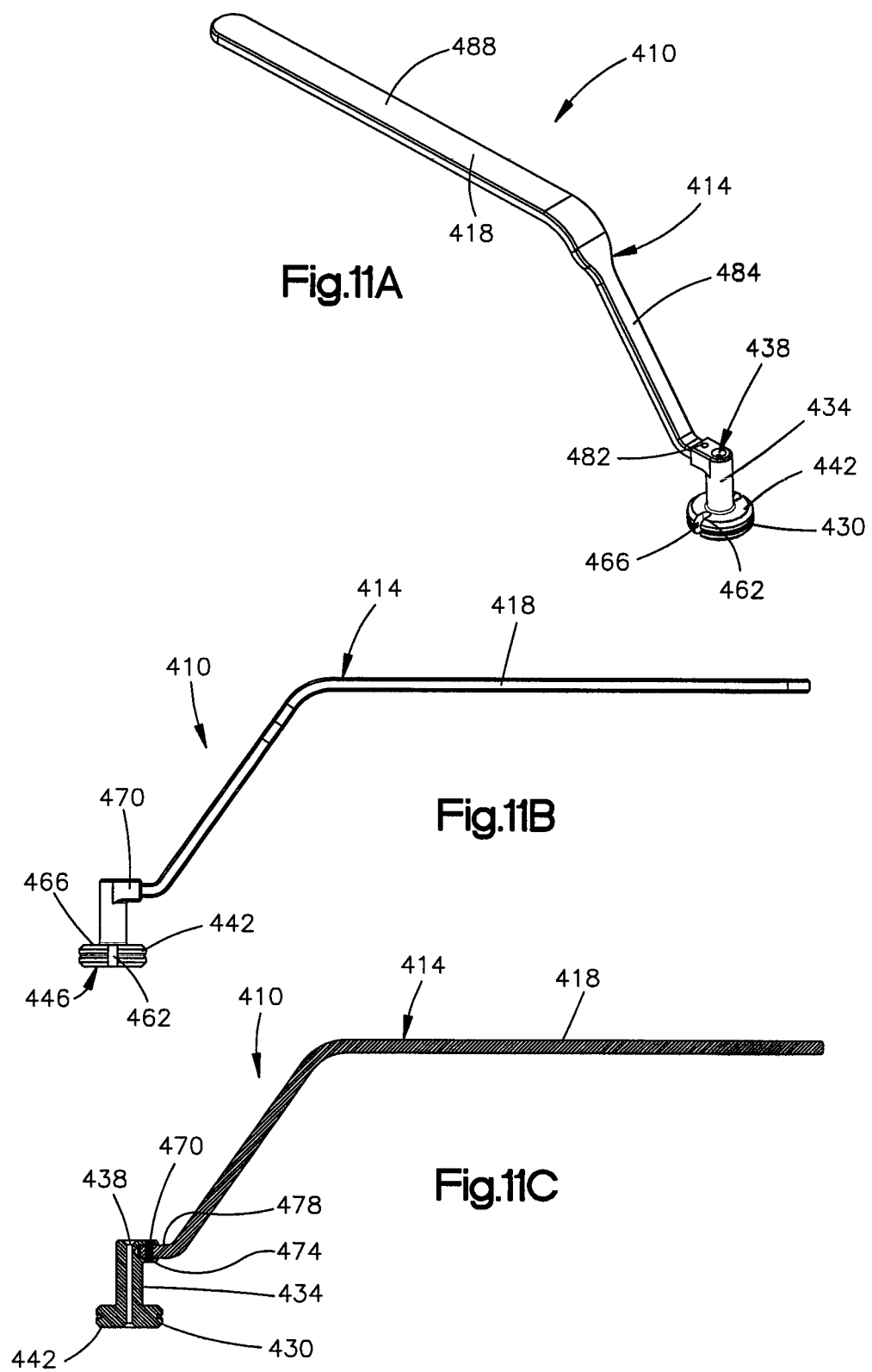

REAMER GUIDE SYSTEMS AND METHODS OF USE

BACKGROUND

Arthrodesis is an operation for fusing two or more bones together. Such an operation is performed to relieve pain caused by a fracture or arthritis. For example, many individuals suffer from wrist arthrosis, which may require fusion of the lunate, the capitate, the hamate, and the triquetrum bones.

One method of fusing these four bones together includes the step of milling out a part of each bone in order to implant a fusion plate. The fusion plate is configured to connect all four bones together by means of screws, so that the four bones can fuse together. During the milling step, however, the four bones have a tendency to elastically move apart from each other due to the force with which the milling reamer is pushed towards the bones. The separation of the bones during the milling may lead to an inaccurately milled countersink. When the fusion plate is to be positioned within the countersink, the diameter of the plate may be bigger than the countersink once the bones move elastically back towards each other.

Moreover, with the current methods, it may be difficult to find the proper location at which the bones are to be milled by the reamer. This is because the countersink is typically made free hand without the use of guides or other aids.

SUMMARY

A reamer guide system may include a reamer guide that is configured to guide a reamer to at least two bones to thereby form a countersink in the at least two bones. The reamer guide may include a guide base having a base body that is configured to be positioned adjacent to at least two bones. The guide base may define a guide aperture that extends through the base body and is configured to receive a reamer and directs the reamer towards the at least two bones when the base body is positioned adjacent to the at least two bones. The guide base may also define at least two bores that extend through the base body at a location so as to be aligned with each of the at least two bones, respectively, when the base body is positioned adjacent to the at least two bones. Each bore may be configured to receive respective temporary fixation elements configured to secure to the at least two bones, respectively, so as to hold the at least two bones relative to each other as the reamer advances into the at least two bones.

The reamer guide system may also include a positioning aid either alone or in combination with the reamer guide. The positioning aid may include an aid base having an aid body that is configured to be positioned adjacent to at least two bones, a handle attachment member that extends from the aid base, and a locating bore that extends through both the member and the aid body. The locating bore may be configured to receive a temporary fixation element. The positioning aid may also include at least two positioning apertures extending through the aid body. Each positioning aperture may be configured to receive a re-positioning device that is capable of repositioning a respective one of the at least two bones.

The positioning aid may be provided as a kit along with a reamer. In such a kit the positioning aid may include an aid base having an aid body that is configured to be positioned adjacent to at least two bones, a member extending from the aid base, and a locating bore that extends through both the member and the aid body. The locating bore may be sized and configured to receive a locating element that is capable of engaging a target location. The reamer may include a reamer body that is configured to mill into bone, and a bore that extends through the reamer body. The bore may be configured to receive the locating element subsequent to the locating element engaging the target location and the positioning aid being removed, such that the reamer is guided along the locating element toward the target location.

A method of reaming a countersink into at least two bones is also disclosed. In that regard a positioning aid may initially be placed onto at least two bones. The positioning aid may include an aid base, a member extending from the aid base, and a locating bore extending through both the member and the aid base. A locating element may be inserted through the locating bore and a distal end of the locating element may be temporarily coupled to a target location adjacent to at least one of the at least two bones. The positioning aid may be removed such that the locating element remains coupled to the target location. A reamer may be positioned proximate to the at least two bones. The reamer may include a reamer body and a bore extending through the reamer body. The bore may be configured to receive the locating element to thereby guide the reamer to the target location. Once positioned, the reamer may ream a countersink into the at least two bones.

BRIEF DESCRIPTION OF THE DRAWINGS

The foregoing summary, as well as the following detailed description of a preferred embodiment of the application, will be better understood when read in conjunction with the appended drawings. For the purposes of illustrating the reamer guide systems and methods of the present application, there is shown in the drawings a preferred embodiment. It should be understood, however, that the application is not limited to the precise arrangements and instrumentalities shown. In the drawings:

FIG. 1A is a perspective view of a reamer guide system constructed in accordance with one embodiment, the reamer guide system including a reamer guide positioned against, and temporarily coupled to a lunate, a capitate, a hamate, and a triquetrum of a wrist, and configured to receive a reamer;

FIG. 1B is a perspective view of the wrist shown in FIG. 1A with the reamer guide system and reamer removed for clarity;

FIG. 2A is a perspective view of the reamer guide shown in FIG. 1A, the reamer guide having a guide base that defines a guide aperture configured to receive the reamer;

FIG. 2B is a top plan view of the reamer guide shown in FIG. 2A;

FIG. 2C is a side elevational view of the reamer guide shown in FIG. 2A;

FIG. 4A is a sectional side elevation view of the reamer guide shown in FIG. 2A temporarily coupled to two of the bones shown in FIG. 1B;

FIG. 4B is a sectional side elevation view of the reamer shown in FIG. 3A milling out a countersink into the bones through the guide aperture of the reamer guide shown in FIG. 4A;

FIG. 6A is a perspective view of the guide system shown in FIG. 1A showing the reamer guide temporarily attached to the lunate, the capitate, the hamate, and the triquetrum of the wrist shown in FIG. 1B, and the reamer positioned above the guide aperture of the reamer guide;

FIG. 6B is a perspective view of the guide system shown in FIG. 6A, showing the reamer advanced into the guide aperture of the reamer guide to form a countersink in the lunate, the capitate, the hamate, and the triquetrum of the wrist;

FIG. 6C is a sectional side elevation view of the guide system shown in FIG. 6C, showing the fusion plate placed into the countersink through the guide aperture of the reamer guide;

FIG. 6D is a sectional side elevation view of the fusion plate shown in FIG. 6D attached to the lunate, the capitate, the hamate, and the triquetrum;

FIG. 7 is a perspective view of reamer guide system constructed in accordance with another embodiment, the reamer guide system including a drill guide system, and a positioning aid temporarily coupled to the drill guide system, the positioning aid positioned against the lunate, the capitate, the hamate, and the triquetrum of the wrist, the positioning aid having an aid base, a handle attachment member extending from the aid base, and a locating bore extending through both the aid base and the aid member, the locating bore configured to receive a temporary fixation element that provides a locating element;

FIG. 8A is a perspective view of the positioning aid shown in FIG. 7;

FIG. 8B is a bottom plan view of the positioning aid shown in FIG. 8A;

FIG. 8C is a sectional side elevation view of the positioning aid shown in FIG. 8B through the line 8C-8C;

FIG. 10A is a perspective view of the guide system shown in FIG. 7 showing the positioning aid temporarily attached to the drill guide of the drill guide system, the positioning aid positioned adjacent to the lunate, the capitate, the hamate, and the triquetrum of the wrist;

FIG. 10B is a perspective view of the guide system shown in FIG. 10A, showing the locating element positioned through the locating bore of the position aid into a target location of the wrist that is to be reamed;

FIG. 10C is a perspective view of the guide system shown in FIG. 10B with the positioning aid and drill guide system removed;

FIG. 10D is a perspective view of the guide system shown in FIG. 10C with the locating element extending through the bore of the reamer to thereby guide the reamer to the target location of the wrist;

FIG. 10E is a sectional side elevation view of the guide system shown in FIG. 10D, showing the reamer forming a countersink in the lunate, the capitate, the hamate, and the triquetrum of the wrist;

FIG. 10F is a sectional side elevation view of the fusion plate placed in the countersink formed by the reamer;

FIG. 11A is a perspective view of a positioning aid constructed in accordance with another embodiment, the positioning aid having an aid base, a member extending from the aid base, and a handle coupled to the member;

FIG. 11B is a side elevation view of the positioning aid shown in FIG. 11A;

FIG. 11C is a sectional side elevation view of the positioning aid shown in FIG. 11B.

DETAILED DESCRIPTION

Figure 3A:
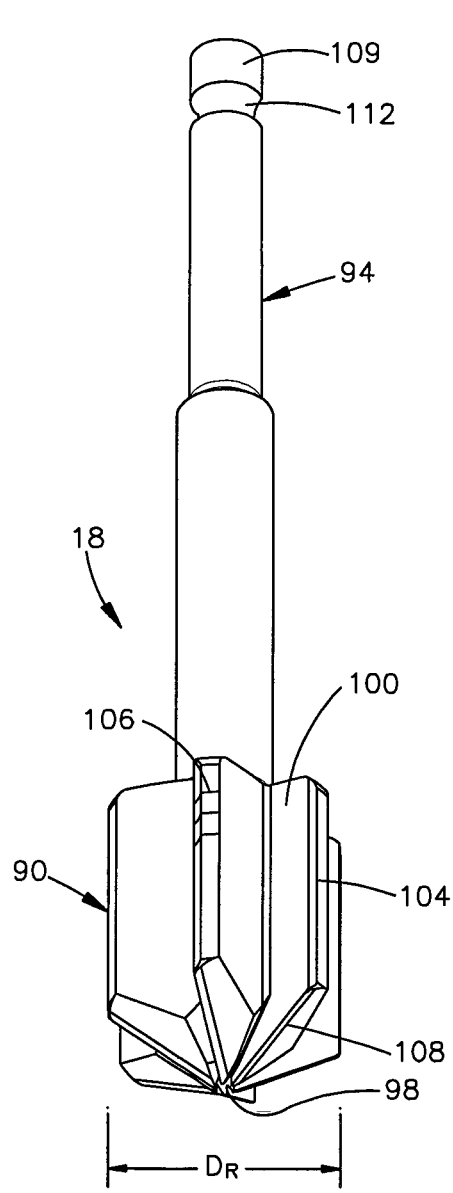
FIG. 3A is a perspective view of the reamer shown in FIG. 1A.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the system and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

As shown in FIG. 1A, a reamer guide system 10 includes a reamer guide 14 that may be used to guide a reamer 18 toward two or more bones to thereby form a countersink (such as countersink 116 shown in FIG. 4B) in the two or more bones. The reamer guide 14 is configured to be temporarily coupled to the two or more bones by a plurality of temporary fixation elements 22 that are removed prior to completion of the surgical procedure, so as to prevent substantial separation of the bones as the reamer 18 is forced against the bones to form the countersink. As shown in FIG. 1A, the reamer 18 is elongate in a longitudinal direction L and is configured to be advanced in the longitudinal direction L through the reamer guide 14. Once the countersink is formed by the reamer 18, a fusion plate (such as fusion plate 26 shown in FIGS. 5A-5D) may be inserted into the countersink 116 and subsequently affixed to the bones to thereby fuse the bones together. As shown in FIG. 1B, the reamer guide system 10 may be used to fuse a lunate 30, a capitate 34, a hamate 38, and a triquetrum 42 of a wrist 46. In such a procedure, the reamer guide 14 may be placed so that the countersink is partially formed in each of the lunate 30, the capitate 34, the hamate 38, and the triquetrum 42, or partially formed in any two of the bones 30, 34, 38, and 42. While the reamer guide system 10 is illustrated as being sized to form a countersink in the bones 30, 34, 38, and 42 of the wrist 46, it should be understood that the reamer guide system 10 may be sized to form a countersink in any two or more bones in the human body.

As shown in FIGS. 2A-2C the reamer guide 14 includes a guide base 50 and a handle 54 that extends from the guide base 50. The handle 54 may be grasped by a user to place the guide base 50 against the bones that are to be reamed. The configuration of the handle 54 and the guide base 50 allows the reamer to ream into the bones without interference from the user.

As shown in FIG. 2A, the guide base 50 includes a base body 56 and a guide aperture 58 that extends through the base body 56. As shown, the base body 56 defines a substantially ring shaped portion 60 having a bottom bone contacting surface 62 that is configured to abut the bones that are to be reamed when the reamer guide 14 is properly positioned. It should be understood, however, that the guide base 50 is not limited to a guide body 56 defining a ring shaped portion 60, and that the guide base 50 may include alternatively shaped bodies 56, such as a body 56 defining a block shaped portion.

As shown in FIGS. 2A and 2B, the guide aperture 58 includes a central axis and extends through the base body 56 such that the guide aperture 58 provides a guide path along the longitudinal direction L to the bones that are to be reamed by the reamer 18. The guide aperture 58 is cylindrical and may have a diameter or alternative dimension D of about 15 mm or about 17 mm. It should be understood, however, that the guide aperture 58 may have any desired dimension D depending on the procedure being performed and the bones being reamed.

As best shown in FIG. 2B, the guide base body 56 also defines four radial extensions 70 that extend radially out from the ring shaped portion 60. As shown, the extensions are spaced equidistant from each other about the ring shaped portion 60. Therefore, each extension 70 may extend out from the ring shaped portion 60 such that each extension 70 is opposed to another extension 70 about the ring shaped portion 60. This configuration allows each extension 70 to be positioned over a respective bone of the four bones that are to be reamed, when the bottom bone contacting surface 62 is abutting the bones. As shown in FIG. 2B, each extension 70 defines two bores 74 that extend through the base body 56. Each extension 70 has two bores 74 so that at least one of the bores 74 but not necessarily both extends through to one of the bones that is to be reamed when the reamer guide 14 is properly positioned. The bores 74 may be equidistantly spaced and each bore 74 of the extensions 70 is configured to receive a respective temporary fixation element 22 such that the fixation elements 22 can extend through the bores 74 and to the bones that are to be reamed. The fixation elements 22 may each be a Kirschner wire (k-wire), pin or other device capable of extending through the bores 74 and temporarily coupling to the bones. Therefore, the bores 74 may define K-wire holes having a diameter that is substantially equal to the diameter of the K-wires. As shown each bore has a diameter or alternative dimension that is less than the diameter of the guide aperture, and each bore 74 has a central axis that is substantially parallel to the guide aperture central axis. Though it should be understood that the central axes of the bores 74 may extend obliquely to the central axis of the guide aperture 58.

In use, the guide base 50 should be positioned over the bones such that a bore 74 of a respective extension 70 is positioned over one of the bones that is to be reamed. When the temporary fixation elements 22 are coupled to the respective bones through the bores 74, the bones will be held in place when the reamer 18 is forced against the bones, to thereby prevent substantial separation of the bones while reaming.

As shown in FIG. 2C, the handle 54 includes an angled portion 80 that extends from the guide base 50 at a desired angle, and a handle portion 84 that extends out from a proximal end of the angled portion 80. As shown in FIG. 2C, the angled portion 80 extends out from the guide base 50, and the handle portion 84 extends from the angled portion 80 such that the guide base 50 will not be interfered with as the user holds and positions the reamer guide 14.

Figure 3B:
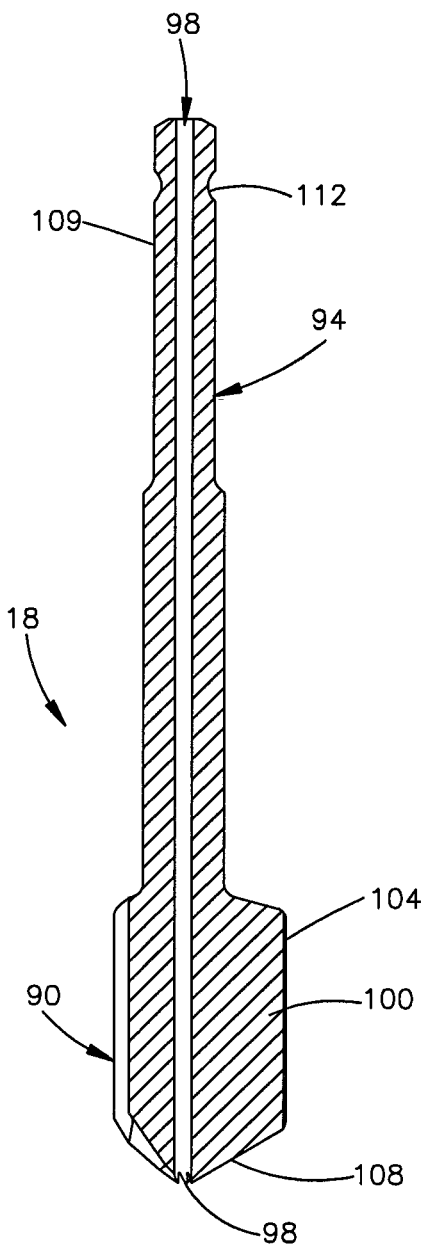
FIG. 3B is a sectional side elevation view of the reamer shown in FIG. 3A.

As shown in FIGS. 3A and 3B, the reamer 18 includes a reamer head 90 and a shaft 94 that extends proximally from a proximal end of the reamer head 90. As shown in FIG. 3B, the reamer 18 further includes a bore 98 that extends completely through the reamer head 90 and the shaft 94. As will be described in more detail later, in certain embodiments, the bore 98 is configured to receive a temporary fixation element that extends from a target location that is to be reamed. Therefore, the bore 98 may have a diameter that is substantially equal to the diameter of the temporary fixation element.

As shown in FIG. 3A, the reamer head 90 is substantially cylindrical in shape and has an outer diameter or alternative dimension $D_R$ that is substantially equal to the diameter D of the guide aperture 58 of the reamer guide 14. As shown, the reamer head 90 includes a plurality of radially extending blades 100. Each blade 100 includes a flat guide portion 104 and an angled cut portion 108 that extends from a distal end of the flat guide portion 104 and radially inward toward the bore 98. As shown, the angled cut portions 108 each terminate at the bore 98. The blades 100, and in particular the angled cut portions 108, are configured to mill or otherwise ream out bones as the reamer 18 is advanced into the bones to thereby form a countersink in the bones.

As best shown in FIG. 3A, each blade 100 further defines a plurality of markings 106 on a proximal portion of the flat guide portion 104. The markings 106 illustrate to the operator how far the reamer 18 has reamed into the bones. Each marking 106 may be spaced apart from an adjacent marking 106 by about 2 mm or other distance as desired. The markings 106 may be positioned such that they are a specific distance from a proximal end of the shaft 94. Therefore, the operator will know the distance the reamer 18 has traveled as the reamer 18 is advanced through the guide aperture 58 of the reamer guide 14.

As shown in FIG. 3A, the shaft 94 is cylindrical and extends proximally from the reamer head 90. As shown, the shaft 94 includes a proximal coupling 109 that is configured to be received by a drive or other extension that ultimately attaches to the drive. As shown, the coupling 109 defines a recess or groove 112 that is configured to be engaged by a projection of the drive or extension to thereby lock the reamer 18 to the drive. The drive may be a manually operated drive or a drive powered by a battery or alternative power source.

As shown in FIGS. 4A and 4B, the reamer guide 14 may be positioned against and temporarily coupled to at least two bones with temporary fixation elements 22. As shown in FIG. 4B, the reamer 18 may be advanced within the guide aperture 58 of the reamer guide 14 to thereby form a countersink 116 within the bones. As shown, the reamer 18 is configured to bore into upper surfaces 118 of the bones along the longitudinal direction L and at a trajectory that is substantially perpendicular to the surface 118 of the bones. The countersink 116 that is formed, is configured to receive the fusion plate 26 such that the fusion plate 26 lies below the upper surfaces 118 of the bones.

Figure 5B:
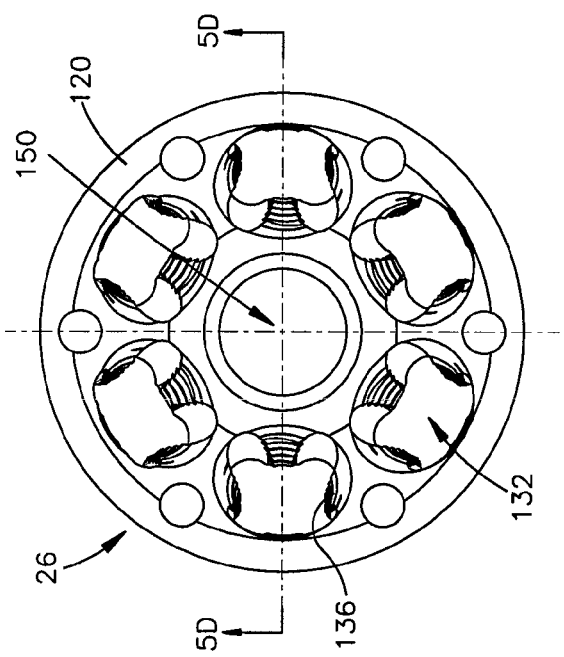
FIG. 5B is a top plan view of the fusion plate shown in FIG. 5A.
Figure 5D:
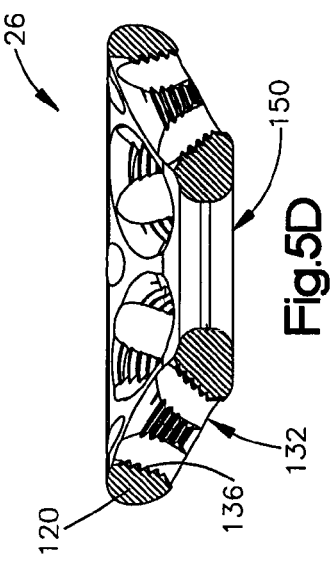
FIG. 5D is a sectional side elevation view of the fusion plate shown in FIG. 5B through the line 5D-5D.
Figure 5A:
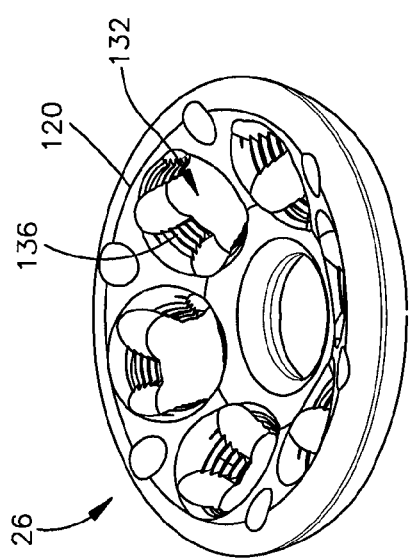
FIG. 5A is a perspective view of a fusion plate that is configured to be positioned within a countersink that is milled into at least two bones, the fusion plate having a plurality of fixation element receiving bores.
Figure 5C:
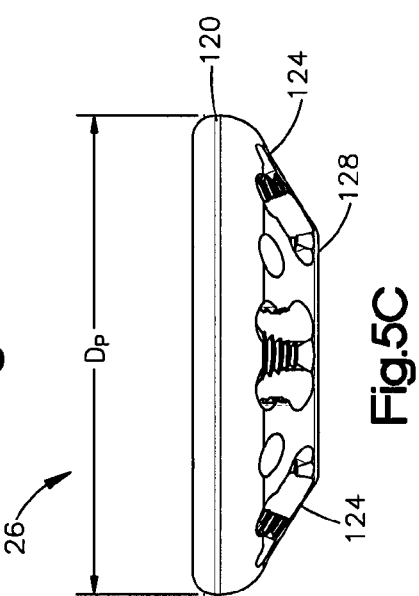
FIG. 5C is a side elevation view of the fusion plate shown in FIG. 5A.

As shown in FIGS. 5A-5D, the fusion plate 26 includes a plate body 120 that is substantially circular and bowl shaped. The plate body 120 has a diameter or alternative dimension $D_P$ that is substantially equal to the diameter $D_R$ of the reamer head 90. The plate 26 may be made from a biocompatible material such as titanium. As shown in FIG. 5C, the plate body 120 defines a beveled lower surface having an angled portion 124 that terminates into a substantially flat portion 128. The beveled lower surface is substantially identical to the profile of the reamer head 90 Therefore, the angled portion 124 extends at an angle so that the plate 26 can sit flush within the countersink 116 formed by the reamer 18. As shown in FIGS. 5A and 5B, the plate 26 further includes a plurality of fixation element receiving bores 132 that extend through the angled portion 124 of the plate body 120. Each bore 132 defines internal threads 136 that are configured to engage external threads defined by a fixation element 140 (as shown in FIG. 6D).

As best shown in FIG. 5D, the bores 132 are conical and are configured to receive a head 144 of the fixation element 140. The conical shape may prevent the fixation element 140 from backing out of the bore 132 after the fixation element 140 has affixed the plate 26 to the milled out bones. In the illustrated embodiment, the plate 26 includes six bores 132, though it should be understood that more or less bores 132 may extend through the plate body 120 depending on the size of the plate 26. Moreover, while the plate 26 is illustrated as being circular and substantially bowl shaped, it should be understood that the plate 26 may have alternative designs as desired.

As shown in FIG. 5B, the fusion plate 26 may also include a central aperture 150 that extends through the center of the plate body 120. The central aperture 150 may help an individual (i.e. surgeon) that needs or desires to inspect the bone fusion process during the healing phase.

In operation and in reference to FIGS. 6A-6D the reamer guide system 10 may be used to form a countersink 116 in the lunate 30, the capitate 34, the hamate 38, and the triquetrum 42 of a wrist 46. In such an operation, the reamer guide 14 may be positioned such that the bone contacting surface 62 of the guide base 50 is abutting the four wrist bones 30, 34, 38, and 42 and at least one of the bores 74 of each extension 70 is positioned over a respective one of the four bones 30, 34, 38, and 42. A temporary fixation element 22 may then be inserted through each bore 74 and coupled to a respective one of the four bones. At this point, each bone is effectively coupled to the reamer guide 14.

As shown in FIG. 6B, the reamer 18 may then be advanced through the guide aperture 58 along the longitudinal direction L and into the four bones 30, 34, 38, and 42 to thereby form the countersink 116. As shown, the guide aperture 58 guides the reamer 18 such that the reamer 18 is substantially perpendicular to the upper surfaces of the four bones being reamed. As the reamer is being forced into the bones 30, 34, 38, and 42, the temporary fixation elements 22 prevent the bones from substantially separating or otherwise moving away from each other. Therefore, when the temporary fixation elements 22 are removed, the diameter of the countersink 116 will remain substantially unchanged.

As shown in FIG. 6C, once the countersink 116 is formed, the fusion plate 26 may be inserted through the guide aperture 58 of the reamer guide 14 and into the countersink 116. As shown, the fusion plate 26 lies within the countersink 116 such that the fusion plate 26 is at least flush with the upper surfaces 118 of the bones 30, 34, 38, and 42 (i.e. tissue that will lie over the bone during joint movement). Because the plate 26 does not protrude above the upper surfaces 118 of the bones, the plate 26 will not interfere or otherwise irritate tissue that lies above the bones 30, 34, 38, and 42. As shown in FIG. 6D, the fixation elements 140 may then be inserted through respective bores 132 of the plate 26 and into the four bones 30, 34, 38, and 42 to thereby affix the plate 26 to the bones and fuse them together.

In another embodiment and in reference to FIG. 7, a reamer guide system 210 may include a positioning aid 214 that is configured to locate a target location 218 (see FIG. 1B) that is adjacent to two or more bones that are to be reamed by the reamer 18. In this regard, the target location 218 may be a location on one of the bones to be reamed or it may be a location between the bones that are to be reamed. As shown in FIG. 7, the positioning aid 214 may be temporarily coupled to a first drill guide 220 of a drill guide system 221 that is temporarily used as a handle to properly position the positioning aid 214 over the bones that are to be reamed. Once the positioning aid 214 is properly positioned, a temporary fixation element 222 constructed substantially as described above with respect to the fixation elements 22 may be inserted or otherwise passed through the drill guide 220 and the positioning aid 214 toward the target location 218. The fixation element 222 may be temporarily coupled to the target location 218 so as to define a locating element that is configured to guide the reamer 18 along a guide path to the bones to be reamed.

As shown n FIGS. 8A-8C, the positioning aid 214 includes an aid base 230 and a handle attachment member 234 that extends proximally at a non-zero angle (e.g. substantially perpendicular) from an upper surface of the aid base 230. In the illustrated embodiment, the member 234 is tubular, though it should be understood that the member 234 may include other configurations as desired. As shown, the positioning aid 214 also includes a locating bore 238 that extends longitudinally through both the aid base 230 and the member 234. The locating bore 238 is at least partially sized and configured to receive the temporary fixation element 222 such that the locating element 222 can extend through the locating bore 238 and into the target location 218.

As shown in FIGS. 8A and 8B, the aid base 230 includes a base body 242 that defines a bottom surface 246 that is configured to face the underlying bone and contact the underlying bone as desired. The bone contacting surface 246 is configured to abut the bones that are to be reamed by the reamer 18 when the positioning aid 214 is properly positioned over the target location 218. As shown in FIGS. 8B and 8C, the base body 242 is cylindrical and defines a recess 250 that extends continuously around a side surface of the base body 242. As shown in FIG. 8C, the aid base 230 further includes a metal ring 254 that extends substantially around the base body 242 within the recess 250. The aid base 230 is made of a biocompatible material and maybe radiolucent. The metal ring 254 is radiopaque and allows the positioning aid 214 to be positioned using an x-ray device. Therefore, the user can follow the positioning aid 214 on an x-ray machine to make sure that the positioning aid 214 is properly positioned over the target location 218. In this way the aid base 230 can be said to be radiopaque. Though it should be understood that the base body 242 itself may be radiopaque so that the positioning aid 214 may be positioned under x-ray.

As shown in FIGS. 8A and 8C, the aid base 230 further includes four positioning apertures 262 that extend through the aid body 242. Each positioning aperture 262 extends through the body 242 such that each aperture 262 is capable of being positioned over a respective bone that is to be reamed out by the reamer 18. Once the positioning aid 214 has been positioned over the target location 218 so that each aperture 262 is over a respective bone that is to be reamed, the apertures 262 may (if needed) each receive a re-positioning device (such as a pin or k-wire) that is configured to re-position a respective one of the bones. That is, if one of the bones that is to be reamed is not correctly positioned, the re-positioning device may be advanced through the aperture 262 of the positioning aid 214 that overlies the bone in need of re-positioning to thereby engage and re-position the bone. In the illustrated embodiment, the apertures 262 are bores that extend through the aid body 242 at angle. It should be understood, however, that the apertures 262 may include configurations other than bores. For example, the apertures 262 may define slots as shown in the embodiment described in reference to FIGS. 11A-11C.

As shown in FIG. 8B, the aid base 230 has a diameter or alternative dimension $D_P$ that is substantially equal to the diameter D of the guide aperture 58 defined by the reamer guide 14. Therefore, in embodiments where the positioning aid 214 is used in conjunction with the reamer guide 14, the aid base 230 of the positioning aid 214 may fit within the guide aperture 58 of the reamer guide 14. It should be understood, however, that while the aid base 230 is described as being cylindrical, the aid base 230 may have other configurations, as desired. For example, the aid base 230 may define a block.

As shown in FIG. 8C, the locating bore 238 extends longitudinally through both the aid base 230 and the member 234. As shown, the locating bore 238 includes a proximal portion 280 that extends at least partially through the member 234, and a distal portion 284 that extends at least partially through the aid base 230. The proximal portion 280 of the locating bore 238 has a diameter or alternative dimension $D_{L1}$ that is configured to receive a portion of the first drill guide 220 of the drill guide system 221, and the distal portion 284 of the locating bore 238 has a diameter or alternative dimension $D_{L2}$ that is configured to receive the locating element 222. For example, the locating element may be a K-wire, and the locating bore 238 may define a K-wire hole that has a diameter that is substantially equal to the diameter of the K-wire. As shown in FIG. 8C, the proximal portion 280 of the locating bore 238 defines a neck 290 proximate to a distal end of the proximal portion 280. The neck 290 is configured to temporarily couple the first drill guide 220 to the positioning aid 214.

Figure 9A:
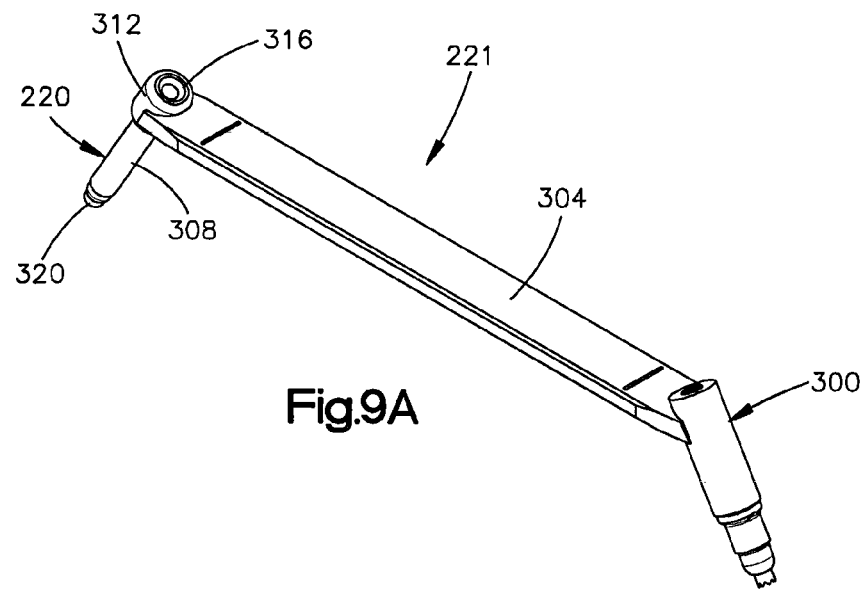
FIG. 9A is a perspective view of a drill guide system having a drill guide that is configured to temporarily couple to the handle attachment member of the positioning aid, the drill guide defining a bore that is configured to receive the locating element and subsequently a drill bit for drilling a bore into bone, the bore configured to receive a fixation element that affixes the fusion plate to bone.
Figure 9B:
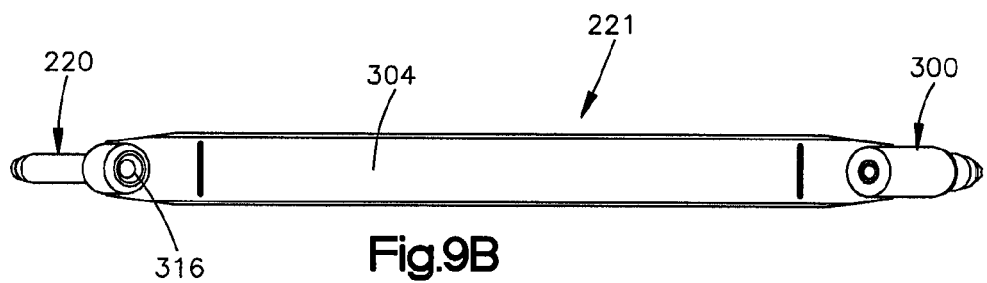
FIG. 9B is a top plan view of the drill guide system shown in FIG. 9A.
Figure 9C:
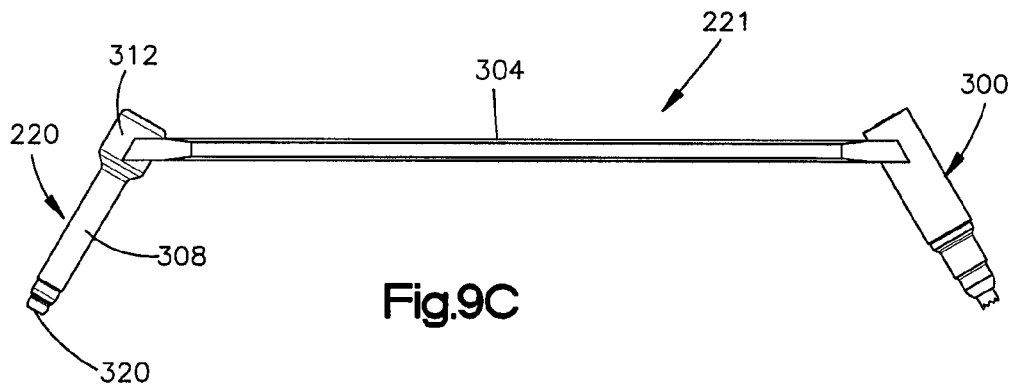
FIG. 9C is a side elevation view of the drill guide system shown in FIG. 9B.

As shown in FIGS. 9A-9C, the drill guide system 221 includes a first drill guide 220 and a second drill guide 300 that are coupled together by a bridge 304. The first drill guide 220 is configured to receive a first drill bit to form a first type of hole in an underlying structure, while the second drill guide 300 is configured to receive a second drill bit to form a second type of hole in an underlying structure. The first drill guide 220 is also configured to couple to the positioning aid 214 so that the drill guide system 221 may be used as a handle to position the positioning aid 214 over the target location 218.

As best shown in FIG. 9C, the first drill guide 220 includes a shaft 308, a head 312 extending from a proximal end of the shaft 308, and a locating bore 316 that extends through both the shaft 308 and the head 312. A distal end of the shaft 308 includes a coupling 320 that is configured to engage the neck 290 defined by the proximal portion 280 of the positioning aid's locating bore 222 to thereby temporarily couple the first drill guide 220 to the positioning aid 214. Referring back to FIG. 7, when the first drill guide 220 is coupled to the positioning aid 214, the locating bore 316 of the first drill guide 220 is configured to align with the distal portion 284 of the locating bore 238 of the positioning aid 214. That is, when the shaft 308 of the first drill guide 220 is disposed within the proximal portion 280 of the locating bore 238, the locating bore 316 of the first drill guide 220 aligns with the distal portion 284 of the positioning aid's locating bore 238. The aligned locating bores 238 and 316 provide a guide path 324 that guides the locating element 222 to the target location 218.

In operation and in reference to FIGS. 10A-10H, the reamer guide system 210 may be used to form a countersink 116 in the lunate 30, the capitate 34, the hamate 38, and the triquetrum 42 of a wrist 46. In such an operation, the positioning aid 214 may initially be coupled to the first drill guide 220 of the drill guide system 221 for positioning over the target location 218. Because the metal ring 254 of the aid base 230 is radiopaque, the proper location of the target location 218 may be determined with the assistance of an x-ray device. Once the target location 218 is determined, the temporary fixation element 222 may be passed through the guide path 324 defined by the locating bores 238 and 316 of the positioning aid 214 and the first drill guide 220 respectively. The temporary fixation element 222 extends through to the target location 218 and is temporary coupled to the target location 218 via a threading or other means.

After the temporary fixation element 222 is coupled to the target location 218, the positioning aid 214 and drill guide system 221 may be removed, leaving the temporary fixation element 222 behind as shown in FIG. 10C. As shown in FIG. 10D, the reamer 18 may then be guided along the temporary fixation element 222 toward the target location 218 to ream out the bones and form the countersink 116. In particular, the temporary fixation element 222 is passed through the bore 98 of the reamer 18 and the reamer is guided to the target location 218 along the temporary fixation element 222 in the longitudinal direction L. As shown in FIG. 10E, the temporary fixation element 222 guides the reamer 18 such that the reamer 18 is substantially perpendicular to the upper surfaces of the four bones being reamed. Moreover, the reamer 18 is configured to ream out the bones while the temporary element 222 is extending through its bore 98 to thereby ensure that the countersink 116 is properly positioned.

As shown in FIG. 10F, once the countersink 116 is formed, the fusion plate 26 may be inserted into the countersink 116. As shown, the fusion plate 26 lies within the countersink 116 such that the fusion plate 26 is at least flush with the upper surfaces 118 of the bones 30, 34, 38, and 42. Because the plate 26 does not protrude above the upper surfaces 118 of the bones, the plate 26 will not interfere or otherwise irritate tissue that lies above the bones 30, 34, 38, and 42.

Figure 10H:
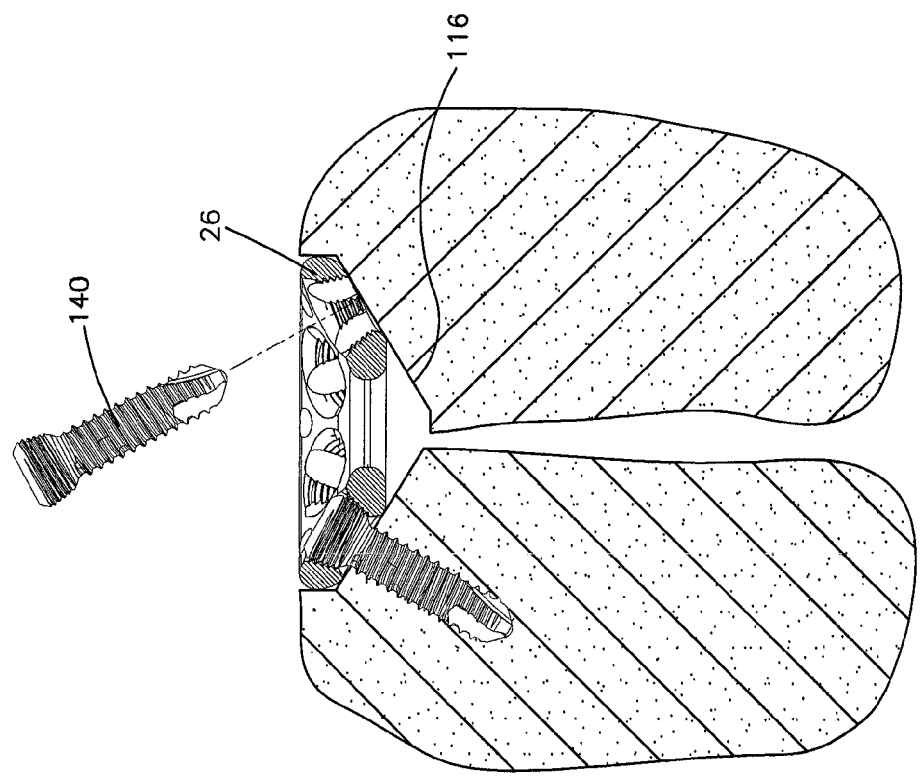
FIG. 10H is a sectional view of the fusion plate shown in FIG. 10G with a fixation element affixing the fusion plate to the wrist.
Figure 10G:
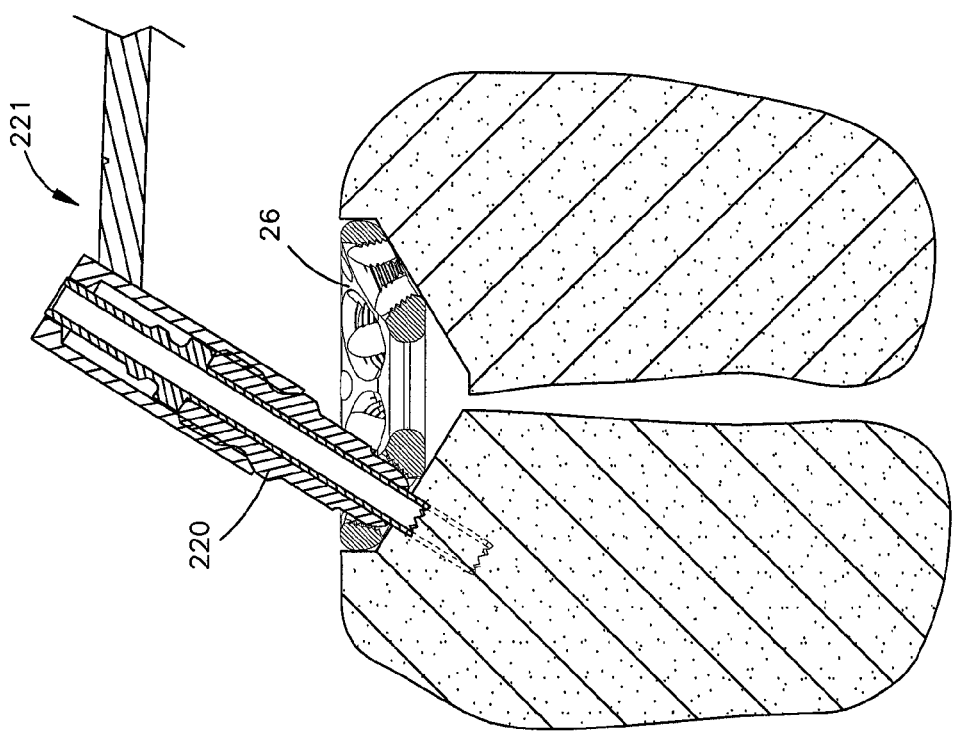
FIG. 10G is a sectional view of the fusion plate shown in FIG. 10F with the drill guide extending into one of the fixation element bores of the fusion plate.

As shown in FIG. 10G, the first drill guide 220 or at least the shaft 308 of the first drill guide 220 is inserted through each bore 132 of the fusion plate 26 that a screw is to be inserted. A drill may then be advanced through the locating bore 316 of the first drill guide 220 and into the bones to form a pre-drilled hole configured to receive a fixation element 140. As shown in FIG. 10H, once the pre-drilled holes are formed in the bones, the fixation elements 140 may be inserted through respective bores 132 of the plate 26 and into the pre-drilled holes formed in each of the four bones 30, 34, 38, and 42 to thereby affix the plate 26 to the bones and fuse them together.

In another embodiment and in reference to FIGS. 11A-11C, a guide system 410 may include a positioning aid 414 that is configured to have a handle 418. As shown, the positioning aid 414 includes an aid base 430, a handle attachment member 434 extending up from the aid base 430, and a locating bore 438 that extends completely through the member 434 and aid base 430. As shown in FIG. 11C, the locating bore 438 has a diameter or alternative dimension that is substantially constant throughout and is configured to receive the locating element 222.

As shown in FIGS. 11A and 11B, the aid base 430 includes a body 442 that defines a bottom or bone contacting surface 446. The bone contacting surface 446 is configured to abut the bones that are to be reamed by the reamer 18 when the positioning aid 414 is properly positioned over the target location 218. As shown in FIGS. 11A and 11B, the aid base 430 further includes a pair of positioning apertures 462 that extend through the aid body 442. Each positioning aperture 462 extends through the body 442 such that each aperture 462 is capable of being positioned over a respective bone that is to be reamed out by the reamer 18. Once the positioning aid 414 has been positioned over the target location 218 so that each aperture 462 is over a respective bone that is to be reamed, the apertures 462 may (if needed) each receive a re-positioning device (such as a pin or k-wire) that is configured to re-position a respective one of the bones. That is, if one of the bones that is to be reamed is not correctly positioned, the re-positioning device may be advanced through the aperture 462 of the positioning aid 214 that overlies the bone in need of re-positioning to thereby engage and re-position the bone. In the illustrated embodiment, the apertures 462 define radial slots 466 that extend through the aid body 442 and to the sides of the aid body 442.

As shown in FIGS. 11A-11C, the member 434 includes a handle coupling 470 proximate to its proximal end. As shown in FIG. 11C, the coupling 470 defines a recess 474 that is configured to receive a coupling 478 defined by the handle 418. As shown in FIGS. 11A and 11C, once the handle coupling 478 is mated with the recess 474 defined by the positioning aid 414, a pin 482 may lock the handle 418 to the positioning aid 414.

As shown in FIG. 11B, the handle 418 includes an angled portion 484 that extends from the member 434 at a desired angle, and a handle portion 488 that extends out from a proximal end of the angled portion 484. As shown in FIG. 11B, the angled portion 484 extends out from the member 434, and the handle portion 488 extends from the angled portion 484 such that the aid base 430 and member 434 will not be interfered with as the user holds and positions the positioning aid 414.

Figure 12:
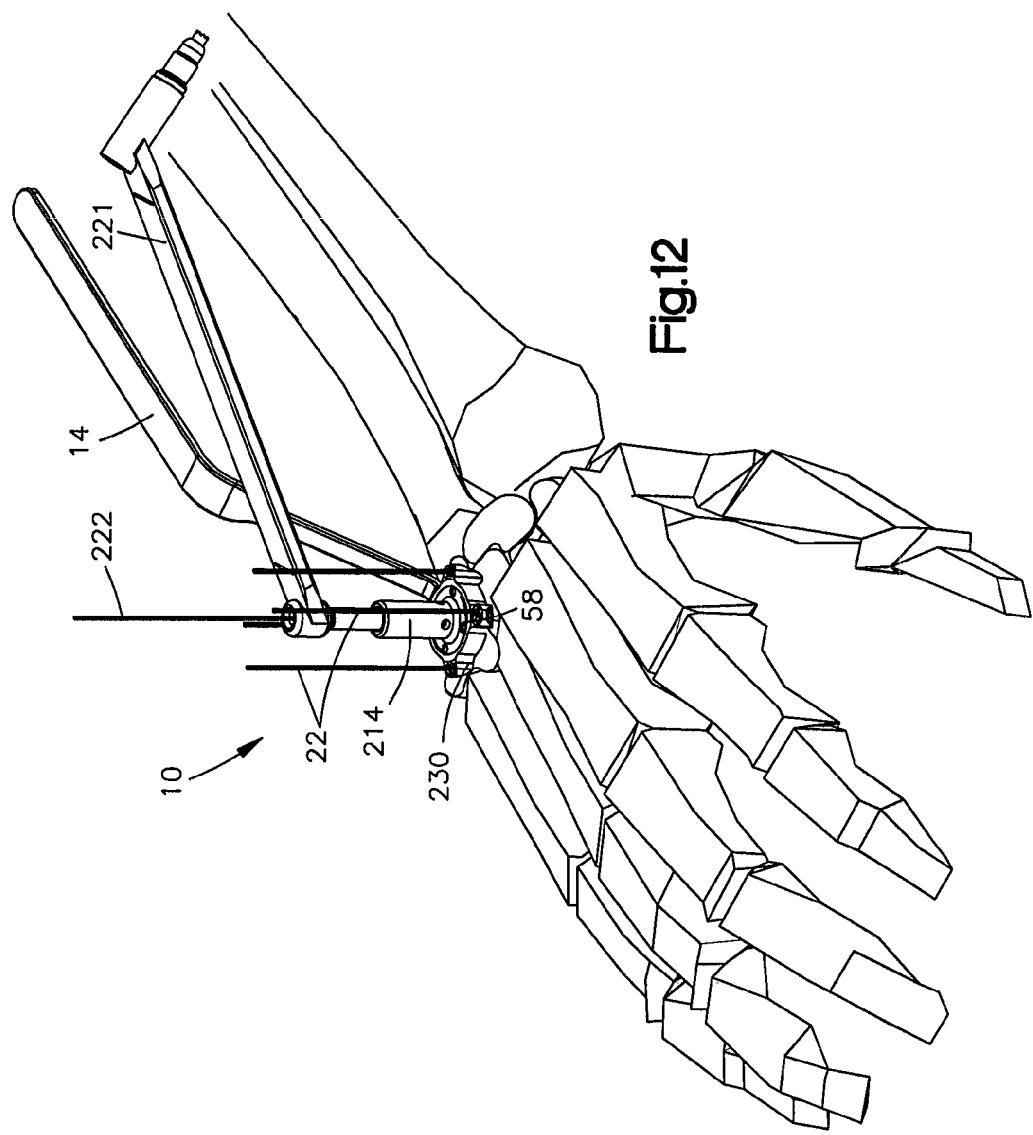
FIG. 12 is a perspective view of a guide system constructed in accordance with another embodiment, the guide system including a reamer guide having a guide aperture, and a positioning aid having an aid base that is configured to be received by the guide aperture of the reamer guide.

While the reamer guide 14 and the positioning aids 214 or 414 have been described as being utilized in separate operations, it should be understood that the reamer guide 14 and positioning aids 214 or 414 may be used together to locate a target location 218 and form a countersink 116, as shown in FIG. 12. As shown, the positioning aid 214 for example, may be used to locate the target location 218 with the assistance of an x-ray machine. Once the locating element 222 has been inserted through the positioning aid 214 and coupled to the target location 218, the positioning aid 214 may be removed. The reamer guide 14 may then be positioned such that the locating element 222 extends through the guide aperture 58 of the reamer guide 14, and the positioning aid 214 may be reinserted so that the aid base 230 of the positioning aid 214 is centrally inside the guide aperture 58 of the reamer guide 14. At this point the reamer guide 14 will be properly positioned, and temporary fixation elements may be inserted to temporarily couple the reamer guide 14 to the four bones. Once coupled to the bones, the positioning aid 214 may be removed and the reamer 18 may be advanced down the locating element 222 to thereby ream out the bones to form the countersink 116.

It should be appreciated that each of the positioning aids 214, 414, reamer guide 14, and reamer 18 may be provided as a kit either alone or in combination with any of the other devices. Furthermore, the kit may be provided with a locating element 222, temporary fixation elements, and/or the drill guide system 221.

It will be appreciated by those skilled in the art that changes could be made to the embodiments described above without departing from the broad inventive concept thereof. For example, the temporary fixation elements may be separate or part of a single unit. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure.

What is claimed:

1. A reamer guide system comprising:
a reamer guide including:
a guide base having a base body that defines a bone contacting surface that is shaped to conform to a lunate, a capitate, a hamate, and a triquetrum when the base body is positioned adjacent to an interface between the lunate, the capitate, the hamate, and the triquetrum, the guide base further defining 1) a guide aperture that extends through the base body and is configured to receive a reamer so as to direct the reamer toward the interface when the base body is positioned adjacent to the interface, and 2) at least four bores that extend through the base body at respective locations so as to be aligned with each of the lunate, the capitate, the hamate, and the triquetrum, respectively, when the base body is positioned adjacent to the interface,
wherein each bore is configured to receive respective temporary fixation-element and guides the respective temporary fixation element into securement with a respective one of the lunate, the capitate, the hamate, and the triquetrum so as to retain the lunate, the capitate, the hamate, and the triquetrum relative to each other as the reamer advances into the interface.

2. The reamer guide system of claim 1, wherein the bores have a cross section less than that of the guide aperture.

3. The reamer guide system of claim 2, wherein each cross-section comprises a diameter.

4. The reamer guide system of claim 1, wherein the guide aperture extends along a central axis, and the bores extend along respective central axes that extend parallel to the central axis of the guide aperture.

5. The reamer guide system of claim 1, wherein the bores are equidistantly spaced about the base body.

6. The reamer guide system of claim 1, wherein the reamer guide includes eight bores that extend through the base body, such that at least two bores extends to each one of the lunate, the capitate, the hamate, and the triquetrum.

7. The reamer guide system of claim 1, wherein the base body defines at least four radial extensions, and each bore extends through a respective extension.

8. The reamer guide system of claim 1, wherein the reamer guide further includes a handle that extends from the guide base.

9. The reamer guide system of claim 1, wherein the bores comprise K-wire holes.

10. The reamer guide system of claim 1, further comprising a positioning aid that is configured to be received by the guide aperture, the positioning aid including:
an aid base that is configured to be positioned adjacent the interface; and
a locating bore that extends through the aid base, wherein the locating bore is configured to receive a temporary fixation element.

11. The reamer guide system of claim 10, further comprising a handle attachment member extending from the aid base, wherein the locating bore further extends through the handle attachment member.

12. The reamer guide system of claim 11, wherein locating bore has a proximal portion sized to receive the handle.

13. The reamer guide system of claim 12, wherein the locating bore further has a second K-wire hole portion sized smaller than the proximal portion.

14. The reamer guide system of claim 11, further comprising a drill guide configured to detachably couple to the handle attachment member.

15. The reamer guide system of claim 11, further comprising a handle that is coupled to the handle attachment member.

16. The reamer guide system of claim 10, further comprising the temporary fixation elements.

17. The reamer guide system of claim 10, wherein the aid base is radiopaque.

18. The reamer guide system of claim 17, wherein the aid base includes a radiolucent base body, and a radiopaque ring.

19. The reamer guide system of claim 10, wherein the locating bore comprises a K-wire hole.

20. The reamer guide system of claim 10, wherein the positioning aid further defines at least one positioning aperture that extends through the aid base and is configured to receive a re-positioning device that is capable of repositioning at least one of the lunate, the capitate, the hamate, and the triquetrum.

21. The reamer guide system of claim 20, wherein the at least one positioning aperture is open to a side wall of the aid base.

22. The reamer guide system of claim 1, wherein the base body defines a bone contacting surface that is shaped to abut to the lunate, the capitate, the hamate, and the triquetrum such that the bone contacting surface abuts the lunate, the capitate, the hamate, and the triquetrum when the base body is positioned adjacent to an interface between the lunate, the capitate, the hamate, and the triquetrum.

23. A method of reaming a countersink into a lunate, a capitate, a hamate, and a triquetrum, the method comprising:
placing a reamer guide adjacent the lunate, the capitate, the hamate, and the triquetrum, the reamer guide including a base body, a guide aperture that extends through the base body, and at least four bores that extend through the base body such that each bore extends to a respective one of the lunate, the capitate, the hamate, and the triquetrum;
inserting a respective temporary fixation element through each bore and into a respect one of the lunate, the capitate, the hamate, and the triquetrum to thereby couple the reamer guide to the lunate, the capitate, the hamate, and the triquetrum;
positioning a reamer within the aperture proximate to the lunate, the capitate, the hamate, and the triquetrum; and
reaming a countersink into the lunate, the capitate, the hamate, and the triquetrum with the reamer such that the reamer guide prevents the lunate, the capitate, the hamate, and the triquetrum from moving away from each other as the reamer advances into the lunate, the capitate, the hamate, and the triquetrum.

24. The method of claim 23, further comprising placing a fusion plate into the countersink.

25. The method of claim 23, further comprising placing a positioning aid onto the lunate, the capitate, the hamate, and the triquetrum, the positioning aid including an aid base, a handle attachment member extending from the aid base, and a locating bore extending through both the handle attachment member and the aid base; and positioning the reamer guide over the aid base of the positioning aid.

26. The method of claim 25, wherein the positioning aid is positioned under x-ray.

* * * * *